(12) United States Patent
Drewes et al.

(10) Patent No.: US 6,437,126 B1
(45) Date of Patent: Aug. 20, 2002

(54) SUBSTITUTED PHENYLURACILS

(75) Inventors: Mark Wilhelm Drewes; Roland Andree, both of Langenfeld (DE); Markus Dollinger, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/841,361

(22) Filed: Apr. 24, 2001

Related U.S. Application Data

(62) Division of application No. 09/194,629, filed as application No. PCT/EP97/02488 on May 15, 1997, now Pat. No. 6,245,714.

(30) Foreign Application Priority Data

May 29, 1996 (DE) .......................... 196 21 311

(51) Int. Cl.$^7$ ................. C07D 239/54; A01N 43/54
(52) U.S. Cl. .................. 544/309; 544/311; 544/312; 544/313
(58) Field of Search ............... 544/311, 312, 544/309, 313; 504/243

(56) References Cited

U.S. PATENT DOCUMENTS

| | | | |
|---|---|---|---|
| 4,979,982 A | 12/1990 | Brouwer et al. | 71/92 |
| 5,084,084 A | 1/1992 | Satow et al. | 71/92 |
| 5,127,935 A | 7/1992 | Satow et al. | 71/92 |
| 5,154,755 A | 10/1992 | Satow et al. | 71/92 |
| 5,169,430 A | 12/1992 | Strunk et al. | 71/92 |
| 5,183,492 A | 2/1993 | Suchy | 514/243 |
| 5,336,663 A | 8/1994 | Wenger et al. | 504/243 |
| 5,356,863 A | 10/1994 | Satow et al. | 504/243 |
| 5,486,521 A | 1/1996 | Brouwer et al. | 514/274 |
| 5,593,945 A | 1/1997 | Andree et al. | 504/243 |
| 5,681,794 A | 10/1997 | Andree et al. | 504/243 |
| 5,700,805 A | 12/1997 | Schäfer et al. | 514/269 |
| 6,245,714 B1 | 6/2001 | Drewes et al. | 504/243 |

FOREIGN PATENT DOCUMENTS

| | | |
|---|---|---|
| DE | 4237920 | 5/1993 |
| WO | 93/06090 | 4/1993 |
| WO | 93/06093 | 4/1993 |

*Primary Examiner*—Mukund J. Shah
*Assistant Examiner*—Hong Liu
(74) *Attorney, Agent, or Firm*—Joseph C. Gil

(57) ABSTRACT

The invention is directed to a process for the preparation of a substituted phenyluracil of the formula:

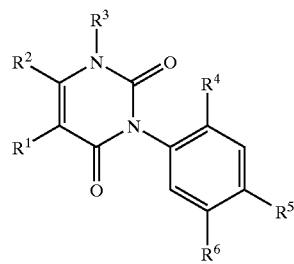

The process broadly comprises reacting a carbonylphenyluracil of the formula:

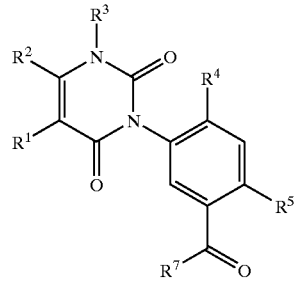

with an amino compound, an alcohol or a mercaptan. The resultant products are useful as herbicides.

1 Claim, No Drawings

SUBSTITUTED PHENYLURACILS

This application is a divisional of Ser. No. 09/194,629, filed Nov. 24, 1998 which is a 371 of PCT/EP97/02488 May 15, 1997, now U.S. Pat. No. 6,245,714.

The invention relates to novel substituted phenyluracils, to processes for their preparation and to their use as herbicides.

It is known that certain substituted uracils have herbicidal properties (cf. DE 4131038, DE 4237920, DE 4329537, EP 408382/U.S. Pat. Nos. 5,084,084/5,127,935/5,154,755, EP 542685, EP 563384, EP 648749, U.S. Pat. Nos. 4,979,982, 5,169,430, WO 91/00278, WO 95/25725). However, these compounds have hitherto not obtained any importance worth mentioning.

This invention, accordingly, provides the novel substituted phenyluracils of the general formula (I)

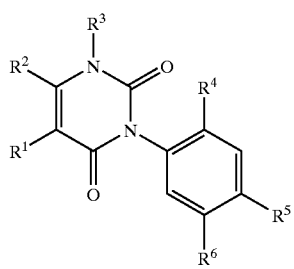
(I)

in which
- $R^1$ represents hydrogen, halogen or optionally substituted alkyl,
- $R^2$ represents optionally substituted alkyl,
- $R^3$ represents hydrogen, amino or represents alkyl, alkenyl or alkinyl, each of which is optionally substituted,
- $R^4$ represents hydrogen, cyano or halogen,
- $R^5$ represents cyano or thiocarbamoyl, and
- $R^6$ represents one of the groups below

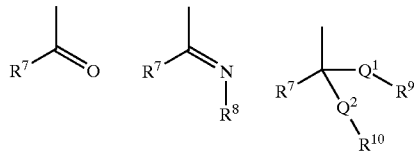

in which
- $Q^1$ and $Q^2$ each represent oxygen or sulphur,
- $R^7$ in each case represents hydrogen or optionally substituted alkyl,
- $R^8$ represents hydrogen, hydroxyl, amino or represents alkyl, alkoxy, alkylamino, dialkylamino, alkylcarbonylamino, alkylsulphonylamino, alkenyl, alkenyloxy, alkinyl, cycloalkyl, cycloalkyloxy, cycloalkylamino, cycloalkylcarbonylamino, cycloalkylsulphonylamino, aryl, aryloxy, arylamino, arylcarbonylamino, arylsulphonylamino, arylalkyl, arylalkoxy, arylalkylamino, each of which is optionally substituted, and
- $R^9$ and $R^{10}$ each represent alkyl.

The novel substituted phenyluracils of the general formula (I) are obtained when (a) alkenylphenyluracils of the general formula (II)

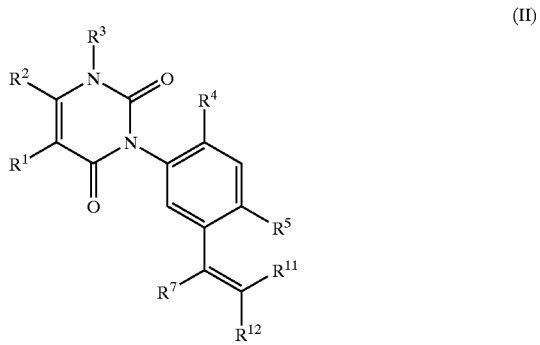
(II)

in which
$R^1$, $R^2$, $R^3$, $R^4$, $R^5$ and $R^7$ are each as defined above and $R^{11}$ and $R^{12}$ each represent hydrogen, cyano, carboxyl or represent alkyl or alkoxycarbonyl, each of which is optionally substituted, are reacted with ozone, if appropriate in the presence of a diluent and if appropriate in the presence of a reaction auxiliary, or when (b) carbonylphenyluracils of the general formula (Ia)

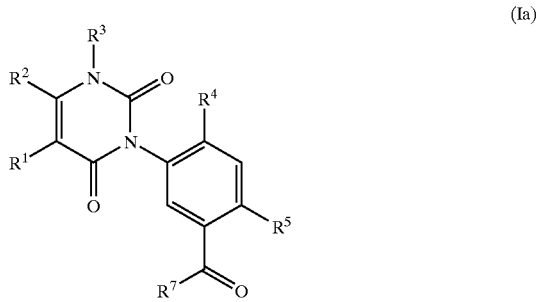
(Ia)

in which
$R^1$, $R^2$, $R^3$, $R^4$, $R^5$ and $R^7$ are each as defined above are reacted with amino compounds of the general formula (III)

$$H_2N-R^8 \quad (III)$$

in which
$R^8$ is as defined above
or with acid adducts of compounds of the formula (II)
if appropriate in the presence of a diluent and if appropriate in the presence of a reaction auxiliary, or when (c) carbonylphenyluracils of the general formula (Ia)

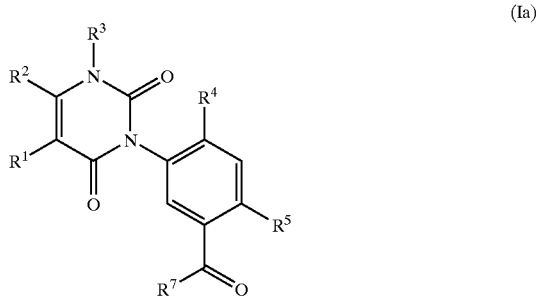
(Ia)

in which
R$^1$, R$^2$, R$^3$, R$^4$, R$^5$ and R$^7$ are each as defined above, are reacted with alcohols and/or mercaptans of the general formulae (IVa) or (IVb)

HQ$^1$R$^9$                              (IVa)

HQ$^2$R$^{10}$                            (IVb)

in which
Q$^1$, Q$^2$, R$^9$ and R$^{10}$ are each as defined above,
if appropriate in the presence of a diluent and if appropriate in the presence of a reaction auxiliary.

The compounds of the general formula (I) can also be converted into other compounds of the general formula (I) in accordance with the above definition using other customary methods, for example by amination and/or alkylation (for example R$^3$: H→NH$_2$, H→CH$_3$), reaction with hydrogen sulphide (for example R$^5$: CN→CSNH$_2$).

The novel substituted phenyluracils of the general formula (I) have strong herbicidal activity.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably represents fluorine, chlorine or bromine and in particular represents fluorine or chlorine.

The invention preferably provides compounds of the formula (I) in which
R$^1$ represents hydrogen, fluorine, chlorine, bromine or optionally fluorine- and/or chlorine-substituted C$_1$–C$_4$-alkyl,
R$^2$ represents optionally fluorine- and/or chlorine-substituted C$_1$–C$_4$-alkyl,
R$^3$ represents hydrogen, amino, represents optionally cyano-, fluorine-, chlorine- or C$_1$–C$_4$-alkoxy-substituted C$_1$–C$_6$-alkyl or represents optionally fluorine- and/or chlorine-substituted C$_2$–C$_6$-alkenyl or C$_2$–C$_6$-alkinyl,
R$^4$ represents hydrogen, cyano, fluorine or chlorine,
R$^5$ represents cyano or thiocarbamoyl, and
R$^6$ represents one of the groups below

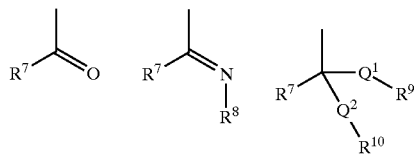

in which
Q$^1$ and Q$^2$ each represent oxygen or sulphur,
R$^7$ in each case represents hydrogen or represents optionally halogen- or C$_1$–C$_4$-alkoxy-substituted C$_1$–C$_4$-alkyl,
R$^8$ represents hydrogen, hydroxyl, amino, represents C$_1$–C$_6$-alkyl, C$_1$–C$_6$-alkoxy, C$_1$–C$_6$-alkylamino, di-(C$_1$–C$_4$-alkyl)-amino, C$_1$–C$_4$-alkylcarbonylamino or C$_1$–C$_4$-alkyl-sulphonylamino, each of which is optionally substituted by halogen, C$_1$–C$_4$-alkoxy or C$_1$–C$_4$-alkoxy-carbonyl, represents C$_2$–C$_6$-alkenyl, C$_2$–C$_6$-alkenyloxy or C$_2$–C$_6$-alkinyl, each of which is optionally substituted by halogen, represents C$_3$–C$_6$-cycloalkyl, C$_3$–C$_6$-cycloalkyloxy, C$_3$–C$_6$-cycloalkylamino, C$_3$–C$_6$-cycloalkyl-carbonylamino or C$_3$–C$_6$-cycloalkylsulphonylamino, each of which is optionally substituted by halogen or C$_1$–C$_4$-alkyl, or represents phenyl, phenoxy, phenylamino, phenylcarbonylamino, phenylsulphonylamino, phenyl-C$_1$–C$_4$-alkyl, phenyl-C$_1$–C$_4$-alkoxy, phenyl-C$_1$–C$_4$-alkylamino, each of which is optionally substituted by halogen, C$_1$–C$_4$-alkyl, C$_1$–C$_4$-halogenoalkyl, C$_1$–C$_4$-alkoxy or C$_1$–C$_4$-halogenoalkoxy, and
R$^9$ and R$^{10}$ each represent C$_1$–C$_4$-alkyl.

The invention in particular relates to compounds of the formula (I) in which
R$^1$ represents hydrogen, fluorine, chlorine, bromine or optionally fluorine- and/or chlorine-substituted methyl or ethyl,
R$^2$ represents optionally fluorine- and/or chlorine-substituted methyl or ethyl,
R$^3$ represents hydrogen, amino, represents methyl, ethyl, n- or i-propyl, n-, i-, s- or t-butyl, each of which is optionally substituted by cyano, fluorine, chlorine, methoxy or ethoxy, or represents optionally fluorine- and/or chlorine-substituted propenyl, butenyl, propinyl or butinyl,
R$^4$ represents hydrogen, fluorine or chlorine,
R$^5$ represents cyano or thiocarbamoyl, and
R$^6$ represents one of the groups below

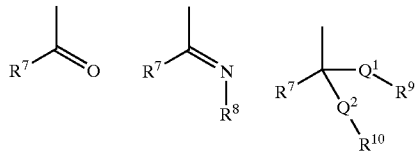

in which
Q$^1$ and Q$^2$ each represent oxygen or sulphur,
R$^7$ in each case represents hydrogen or represents methyl or ethyl, each of which is optionally substituted by fluorine, chlorine, methoxy or ethoxy,
R$^8$ represents hydrogen, hydroxyl, amino, represents methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, dimethylamino, acetylamino, propionylamino, n- or i-butyroylamino, methylsulphonylamino or ethylsulphonylamino, each of which is optionally substituted by fluorine, chlorine, methoxy, ethoxy, methoxycarbonyl or ethoxycarbonyl, represents propenyl, butenyl, propenyloxy, butenyloxy, propinyl or butinyl, each of which is optionally substituted by fluorine, chlorine or bromine, represents cyclopentyl, cyclohexyl, cyclopentyloxy, cyclohexyloxy, cyclopentylaamino, cyclohexylamino, cyclopropylcarbonylamino, cyclobutylcarbonylamino, cyclopentylcarbonylamino, cyclohexylcarbonylamino, cyclopropylsulphonylamino, cyclobutylsulphonylamino, cyclopentylsulphony-lamino or cyclohexylsulphonylamino, each of which is optionally substituted by fluorine, chlorine, bromine, methyl or ethyl, or represents phenyl, phenylamino, phenylcarbonylamino, phenylsulphonylamino, benzyl, benzyloxy or benzylamino, each of which is optionally substituted by fluorine, chlorine, bromine, methyl, ethyl, trifluoromethyl, methoxy, ethoxy, difluoromethoxy or trifluoromethoxy, and $R^9$ and $R^{10}$ each represent methyl or ethyl.

The abovementioned general or preferred radical definitions apply both to the end products of the formula (I) and correspondingly to the starting materials or intermediates required in each case for the preparation. These radical definitions can be combined with each other at will, i.e. including combinations between tile preferred ranges stated.

Examples of the compounds of the formula (I) according to the invention are listed in the groups below.

Group 1

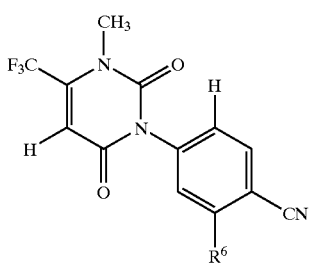

$R^6$ has in this case for example the meanings given in the list below: formyl, acetyl, methyliminomethyl, ethyliminomethyl, n-propyliminomethyl, i-propyliminomethyl, hydroximinomethyl, methoximinomethyl, ethoximinomethyl, n-propoximinomethyl, i-propoximinomethyl, n-butoximinomethyl, 1-methoximino-ethyl, methoxycarbonylmethoximinomethyl, ethoxycarbonylmethoximinomethyl, 1-methoxycarbonylmethoximino-ethyl, 1-ethoxycarbonylmethoximino-ethyl, hydraziminomethyl, methylhydraziminonmethyl, dimethylhydraziminomethyl, acetylhydraziminomethyl, methylsulphonylhydraziminomethyl, allyloximinomethyl, cyclopentyloximinomethyl, cyclohexyloximinomethyl, benzyloximinomethyl, cyclopentylhydraziminomethyl, cyclohexylhydraziminomethyl, phenylhydraziminomethyl, phenylcarbonylhydraziminomethyl, phenylsulphonylhydraziminiomethyl, benzylhydraziminomethyl, dimethoxymethyl, diethoxymethyl.

Group 2

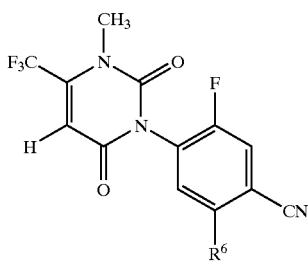

$R^6$ has in this case for example the meanings given above in group 1.

Group 3

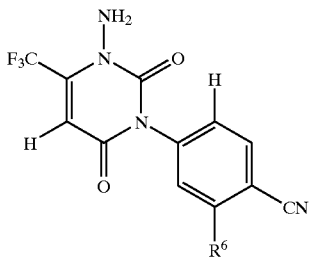

$R^6$ has in this case for example the meanings given above in group 1.

Group 4

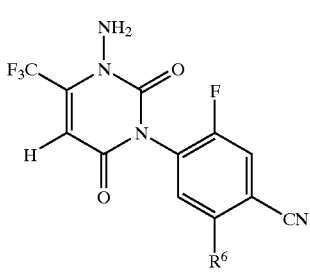

$R^6$ has in this case for example the meanings given above in group 1.

Group 5

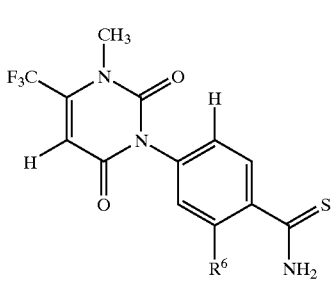

$R^6$ has in this case for example the meanings given above in group 1.

Group 6

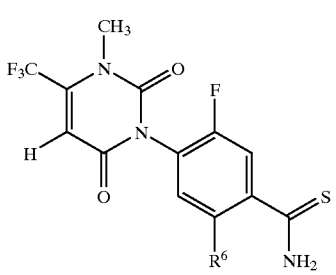

$R^6$ has in this case for example the meanings given above in group 1.

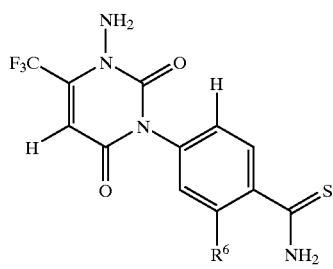

Group 7

$R^6$ has in this case for example the meanings given above in group 1.

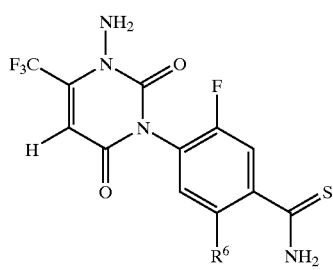

Group 8

$R^6$ has in this case for example the meanings given above in group 1.

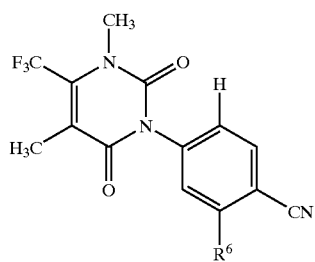

Group 9

$R^6$ has in this case for example the meanings given above in group 1.

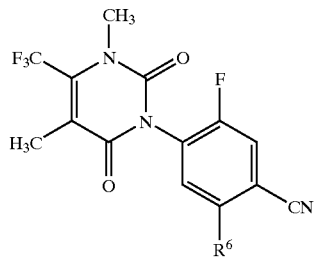

Group 10

$R^6$ has in this case for example the meanings given above in group 1.

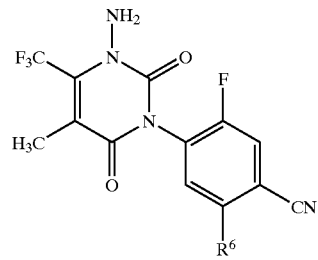

Group 11

$R^6$ has in this case for example the meanings given above in group 1.

Group 12

$R^6$ has in this case for example the meanings given above in group 1.

Group 13

$R^6$ has in this case for example the meanings given above in group 1.

Group 14

$R^6$ has in this case for example the meanings given above in group 1.

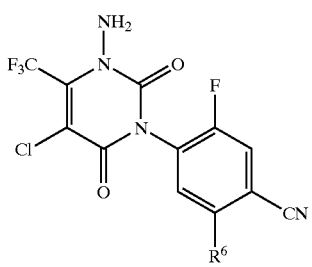

Group 15

$R^6$ has in this case for example the meanings given above in group 1.

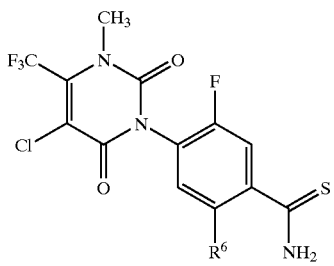

Group 16

$R^6$ has in this case for example the meanings given above in group 1.

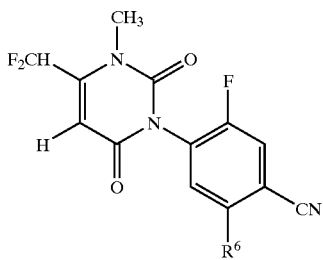

Group 17

$R^6$ has in this case for example the meanings given above in group 1.

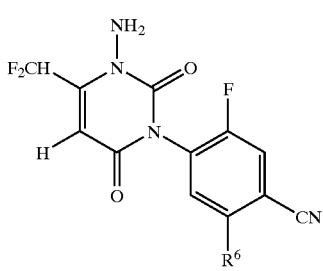

Group 18

$R^6$ has in this case for example the meanings given above in group 1.

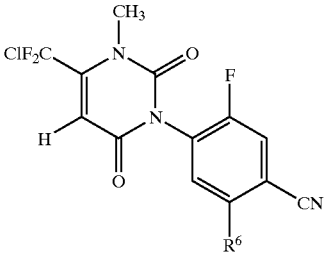

Group 19

$R^6$ has in this case for example the meanings given above in group 1.

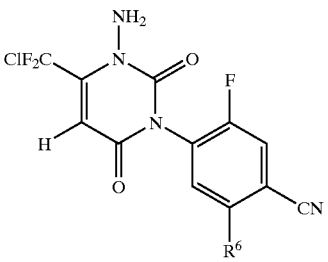

Group 20

$R^6$ has in this case for example the meanings given above in group 1.

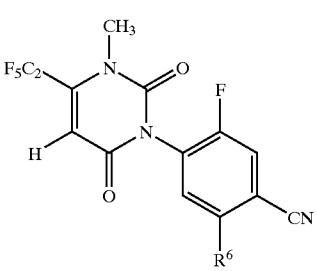

Group 21

$R^6$ has in this case for example the meanings given above in group 1.

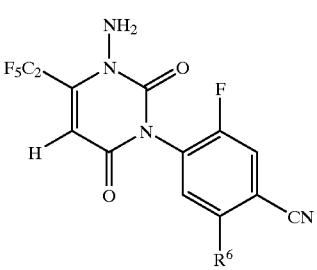

Group 22

$R^6$ has in this case for example the meanings given above in group 1.

Using, for example, 1-[4-cyano-2-fluoro-5-(2-methoxycarbonyl-ethenyl)-phenyl]-3,6-dihydro-2,6-dioxo-3-methyl-4-trifluoromethyl-1(2H)-pyrimidine and ozone as starting materials, the course of the reaction in the process (a) according to the invention can be illustrated by the following equation:

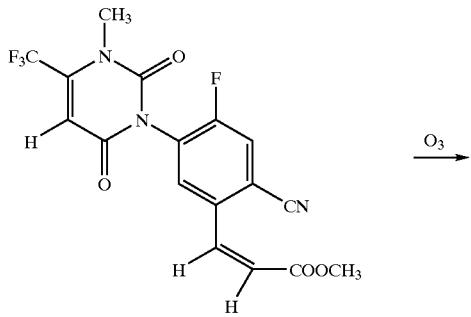

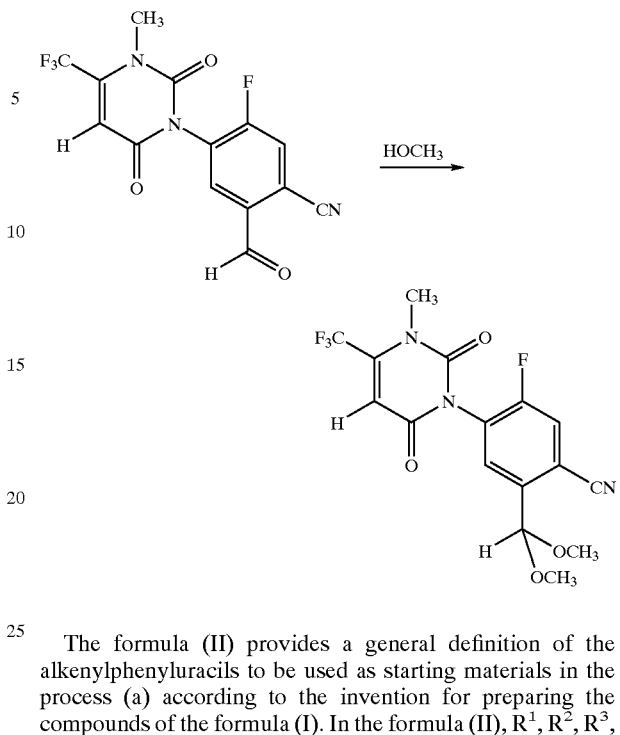

Using, for example, 1-(4-cyano-2-fluoro-5-formyl-phenyl)-3,6-dihydro-2,6-dioxo-3-methyl-4-trifluoromethyl-1(2H)-pyrimidine and O-methyl-hydroxylamine as starting materials, the course of the reaction in the process (b) according to tile invention can be illustrated by the following equation:

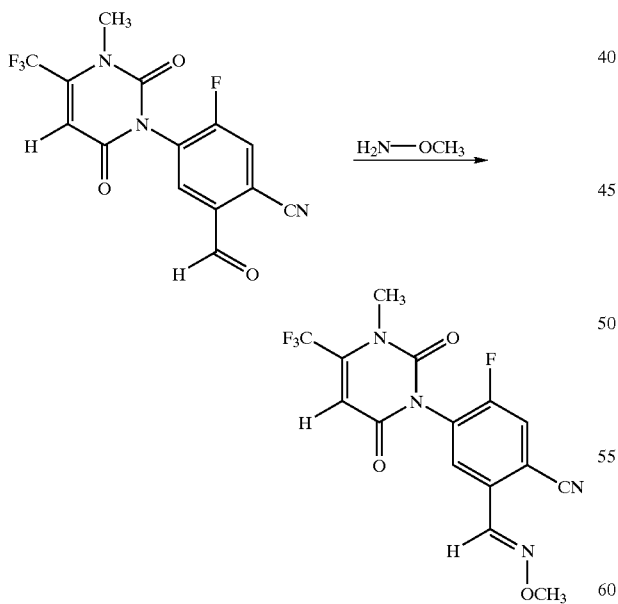

Using, for example, 1-(4-cyano-2-fluoro-5-formyl-phenyl)-3,6-dihydro-2,6-dioxo-3-methyl-4-trifluoromethyl-1(2H)-pyrimidine and methanol as starting materials, the course of the reaction in tile process (c) according to the invention can be illustrated by the following equation:

The formula (II) provides a general definition of the alkenylphenyluracils to be used as starting materials in the process (a) according to the invention for preparing the compounds of the formula (I). In the formula (II), $R^1$, $R^2$, $R^3$, $R^4$, $R^5$ and $R^7$ each preferably or in particular have that meaning which has already been mentioned above, in connection with the description of the compounds of the formula (I) to be prepared according to the invention, as being preferred or as being particularly preferred for $R^1$, $R^2$, $R^3$, $R^4$, $R^5$ and $R^7$, $R^{11}$ and $R^{12}$ preferably represent cyano, carboxyl or $C_1$–$C_4$-alkoxycarbonyl.

The starting materials of the formula (II) have hitherto not been disclosed in the literature; as novel substances they form part of the subject matter of a prior but not prepublished application (cf. DE 19 528 186).

The alkenylphenyluracils of the general formula (II) are obtained when aminophenyluracils of the general formula (V)

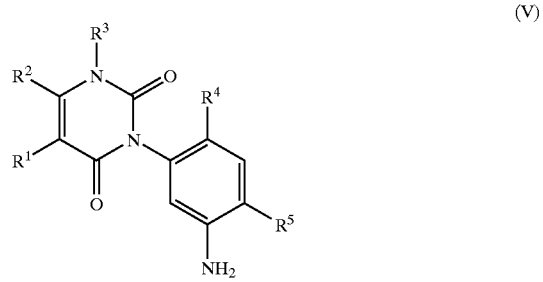

in which $R^1$, $R^2$, $R^3$, $R^4$ and $R^5$ are each as defined above or acid adducts of compounds of the formula (V)

are reacted with an alkali metal nitrite or alkyl nitrite, such as, for example, sodium nitrite, potassium nitrite, methyl nitrite, n- or t-butyl nitrite, and with a hydrogen halide ($HX^1$), such as, for example, hydrogen chloride or hydrogen bromide, or a metal halide, such as, for example, copper(I) chloride or copper(II) chloride, if appropriate in the presence of a diluent, such as, for example, water, acetic acid, acetonitrile and methylene chloride, at temperatures between −20° C. and +10° C., and the resulting diazonium salts of the general formula (VI)

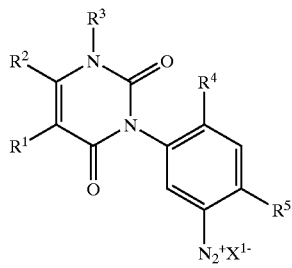
(VI)

in which
R$^1$, R$^2$, R$^3$, R$^4$ and R$^5$ are each as defined above and X$^1$ represents halogen
are reacted with acrylic acid derivatives of the general formula (VII)

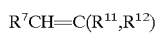
(VII)

in which
R$^7$, R$^{11}$ and R$^{12}$ are each as defined above,
in the presence of hydrogen halides (HX$^1$), such as, for example, hydrogen chloride or hydrogen bromide, if appropriate in the presence of water and if appropriate in the presence of the organic solvent initially used, at temperatures between 0° C. and 50° C., and the resulting products are reacted with acid acceptors, such as, for example, sodium hydride, in tile presence of diluents, such as, for example, N,N-dimethyl-formamide, at temperatures between 0° C. and 100° C. (cf. the Preparation Examples).

The formula (1a) provides a general definition of the carbonylphenyluracils to be used as starting materials in the processes (b) and (c) according to the invention for preparing compounds of the formula (I). In the formula (Ia), R$^1$, R$^2$, R$^3$, R$^4$, R$^5$ and R$^7$ each preferably or in particular have those meanings which have already been mentioned above, in connection with the description of the compounds of the formula (I) according to the invention, as being preferred or as being particularly preferred for R$^1$, R$^2$, R$^3$, R$^4$, R$^5$ and R$^7$.

The starting materials of the formula (Ia) are novel compounds according to the invention; they can be prepared by the process (a) according to tile invention.

The formula (III) provides a general definition of the amino compounds further to be used as starting materials in the process (b) according to the invention for preparing compounds of tile formula (I). In the formula (III), R$^8$ preferably or in particular has that meaning which has already been mentioned above, in connection with the description of the compounds of the formula (I) according to the invention, as being preferred or as being particularly preferred for R$_8$.

The starting materials of the formula (III) are known chemicals for synthesis.

The formulae (IVa) and (IVb) provide a general definition of the alcohols or mercaptans further to be used as starting materials in the process (c) according to the invention for preparing compounds of the formula (I). In the formulae (IVa) and (IVb), Q$^1$, Q$^2$, R$^9$ and R$^{10}$ each preferably or in particular have those meanings which have already been mentioned above, in connection with the description of the compounds of the formula (I) according to the invention, as being preferred or as being particularly preferred for Q$^1$, Q$^2$, R$^9$ and R$^{10}$.

The starting materials of the formulae (IVa) and (IVb) are known chemicals for synthesis.

Suitable diluents for carrying out the processes (a) to (c) according to the invention are especially inert organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

The process (a) according to the invention is carried out in the presence of a reaction auxiliary. Reaction auxiliaries which are preferred here are chemicals having reducing action, such as, for example, zinc dust in acetic acid, hydrogen in the presence of palladium, sodium dithionite and dimethyl sulphide.

When carrying out the process (a) according to the invention, the reaction temperatures can be varied within a relatively wide range. In general, the process (a) is carried out at temperatures between −100° C. and +50° C., preferably between −80° C. and +30° C.

The process (a) according to the invention is generally carried out under atmospheric pressure. However, it is also possible to carry out the process according to the invention under elevated or reduced pressure—generally between 0.1 bar and 10 bar.

In a preferred embodiment of the process (a) according to the invention, the starting material of the formula (II) is initially charged in a diluent and cooled to the temperature required, and ozone is then introduced until the reaction has ended. The cooling bath is removed and the reaction auxiliary is then metered in and tile mixture is stirred at the required temperature until the reaction has ended. Work-up can be carried out in a customary manner (cf. the Preparation Examples).

Suitable reaction auxiliaries for the process (b) according to the invention are generally the customary inorganic or organic bases or acid acceptors. These include preferably alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperdine, 1,4-diazabicyclo[2,2,2]-octane (DABCO), 1,5-diazabicyclo[4,3,0]-non-5-ene (DBN), or 1,8-diazabicyclo[5,4,0]-undec-7-ene (DBU).

When carrying out the process (b) according to the invention, tile reaction temperatures can be varied within a relatively wide range. In general, the process (b) is carried out at temperatures between 0° C. and 150° C., preferably between 10° C. and 120° C.

The process (b) according to the invention is generally carried out under atmospheric pressure. However, it is also possible to carry out the process according to the invention under elevated or reduced pressure - generally between 0.1 bar and 10 bar.

For carrying out the process (b) according to the invention, the starting materials are generally employed in approximately equimolar amounts. However, it is also possible to use one of the components in a relatively large excess. The reaction is generally carried out in a suitable diluent in the presence of a reaction auxiliary, and the reaction mixture is generally stirred for several hours at the temperature required. Work-up is carried out by customary methods (cf. the Preparation Examples).

The process (c) according to the invention is preferably carried out in the presence of a reaction auxiliary. Suitable reaction auxiliaries here are oxidizing agents, such as hydrogen peroxide, and acids, such as, for example, sulphuric acid.

When carrying out the process (c) according to the invention, the reaction temperatures can be varied within a relatively wide range. In general, the process (c) is carried out at temperatures between 0° C. and 120° C., preferably between 10° C. and 100° C.

The process (c) according to the invention is generally carried out under atmospheric pressure. However, it is also possible to carry out the process according to the invention under elevated or reduced pressure—generally between 0.1 bar and 10 bar.

In a preferred embodiment of the process (c) according to the invention, the reaction auxiliary is added to a mixture of the starting material of the formula (Ia) and the alcohol or mercaptan of the formula (IVa) or (IVb), and the reaction mixture is stirred until the reaction has ended. Work-up is carried out by customary methods (cf. the Preparation Examples).

The active compounds according to the invention can be used as defoliants, desiccants, haulm-killers and, especially, as weed-killers. Weeds, in the broadest sense, are all plants which grow in locations where they are undesired. Whether the substances according to the invention act as total or selective herbicides depends essentially on the amount used.

The active compounds according to the invention can be used, for example, in connection with the following plants:

Dicotyledonous Weeds of the Genera

Sinapis, Lepidium, Galiuni, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous Crops of the Genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous Weeds of the Genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous Crops of the Genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with and without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The compounds of the formula (I) according to the invention are particularly suitable for the selective control of monocotyledonous and dicotyleclonous weeds in monocotyledonous and dicotyledonous crops both by the pre- and the post-emergence method.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine encapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use for example organic solvents as auxiliary solvents. Essentially, suitable liquid solvents are: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, suitable solid carriers for granules are: for example crushed and fractionated natural rocks such as calcite, marble, pumice, sepiolite and dolomite, and also synthetic granules of inorganic and organic meals, and also granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, aryl-sulphonates and also protein hydrolysates, suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be used as such or, in their formulations, also as a mixture with known herbicides for the control of weeds, in which case ready-to-use formulations or tank mixes are possible.

Suitable for the mixtures are known herbicides, for example anilides, such as, for example, diflufenican and propanil; arylcarboxylic acids, such as, for example, dichloropicolinic acid, dicamba and picloram; aryloxyalkanoic acids, such as, for example, 2,4 D, 2,4 DB, 2,4 DP, fluroxypyr, MCPA, MCPP and triclopyr; aryloxy-phenoxy-alkanoic esters, such as, for example, diclofop-methyl, fenoxapropethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloroacetanilides, such as, for example, alachlor, acetochlor, butachlor, metazachlor, nietolachlor, pretilachlor and propachlor; dinitroanilines, such as, for example, oryzalin, pendimethialin and trifluralin; diphenyl ethers, such as, for example, acifluorfen, bifenox, fluoroglycofen, fomesafen, halosafen, lactofen and oxyfluorfen; ureas,such as, for example, chlortoluron, diuron, fluometuron, isoproturon, linuron and methabenzthiazuron; hydroxylamines, such as, for example, alloxydim, clethodim,cycloxydim, sethoxydim and tralkoxydim; imidazolinones, such as, for example, imazethapyr, imazamethabenz, imazapyr and imazaquin; nitriles, such as, for example, bromoxynil, dichlobenil and ioxynil; oxyacetamides, such as, for example, mefenacet; sulphonylureas, such as, for example, amidosulfuron, bensulfuron-methyl, chlorimuron-ethyl, chlorsulfuron, cinosulfuron, metsulfuronmethyl, nicosulfuron, primisulfuron, pyrazosulfuron-ethyl, thifensulfuron-methyl, triasulfuron and tribenuron-methyl; thiolcarbamates, such as, for example, butylate, cycloate, di-allate, EPTC, esprocarb, molinate, prosulfocarb, thiobencarb and triallate; triazines, such as, for example, atrazine, cyanazine, simazine, simetryne, terbutryne and terbutylazine; triazinones, such as, for example, hexazinone, metamitron and metribuzin; others, such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied both before and after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

(Process (a))

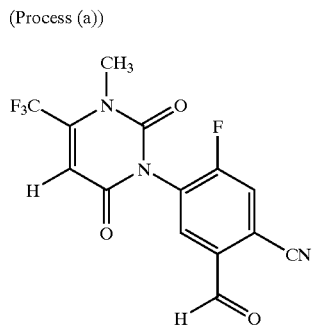

For 45 minutes, ozone is introduced into a mixture of 8.7 g (22 mmol) of 1-[4-cyano-2-fluoro-5-(2-methoxycarbonyl-ethenyl)-phenyl]-3,6-dihydro-2,6-dioxo-3-methyl-4-trifluoromethyl-1(2H)-pyrimidine and 600 ml of metlhylene chloride which had been cooled to −70° C. The cooling bath is then removed and the mixture is admixed with 10 ml of dimethyl sulphide. Once the mixture has warmed to room temperature (approximately 20° C.), the phases are separated and the organic phase is washed with water, dried with sodium sulphate and filtered.

The filtrate is concentrated under water pump vacuum, the residue is digested with diethyl ether and the crystalline product is isolated by filtration with suction.

This gives 7.4 g (99% of theory) of 1-(4-cyano-2-fluoro-5-formyl-phenyl)-3,6-dihydro-2,6-dioxo-3-methyl-4-trifluoromethyl-1(2H)-pyrimidine of melting point 177° C.

Example 2

(Process (b))

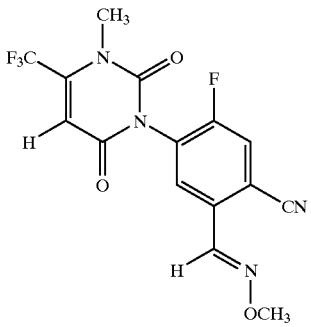

At room temperature (approximately 20° C.), a mixture of 1.0 g (2.9 mmol) of 1-(4-cyano-2-fluoro-5-formyl-phenyl)-3,6-dihydro-2,6-dioxo-3-methyl-4-trifluoromethyl-1(2H)-pyrimidine, 0.25 g (3.0 mmol) of O-methyl-hydroxylamine hydrochloride, 0.25 g (3.0 mmol) of sodium acetate and 20 ml of ethanol is stirred for approximately 90 minutes. The mixture is concentrated under water pump vacuum and the residue is taken up in water, admixed with 2N hydrochloric acid and extracted with diethyl ether. The organic phase is dried with sodium sulphate and filtered. The solvent is then carefully distilled off from the filtrate under water pump vacuum.

This gives 0.8 g (74% of theory) of 1-(4-cyano-2-fluoro-5-methoximinomethylphenyl)-3,6-dihydro-2,6-dioxo-3-methyl-4-trifluoromethyl-1(2H)-pyrimidine of melting point 80° C.

Example 3

(Process (c))

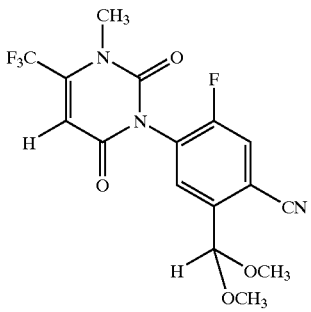

At approximately 10° C., 0.28 g of hydrogen peroxide (30% strength) and 0.59 g of conc. sulphuric acid are mixed, stirred at approximately 20° C. for about 2 hours and then added to a mixture of 1.0 g (2.9 mmmol) of 1-(4-cyano-2-fluoro-5-formyl-phenyl)-3,6-dihydro-2,6-dioxo-3-methyl-4-trifluorometyl-1(2H)-pyrimidine and 20 ml of methanol. The reaction mixture is stirred at room temperature (approximately 20° C.) for about 15 hours, and the crystalline product is isolated by filtration with suction.

This gives 0.70 g (62% of theory) of 1-(4-cyano-2-fluoro-5-dimethoxymethylphlenyl)-3,6-dihydro-2,6-dioxo-3-methyl-4-trifluoromethyl-1(2H)-pyrimidine of melting point 164° C.

By the methods of Preparation Examples 1 to 3 and in accordance with the general description of the preparation processes according to the invention, it is also possible to prepare, for example, the compounds of the formula (I) listed in Table 1 below.

TABLE 1

(I)

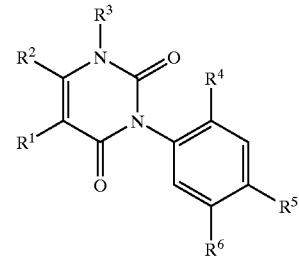

Examples of the compounds of the formula (I)

| Ex. No. | $R^1$ | $R^2$ | $R^3$ | $R^4$ | $R^5$ | $R^6$ | Melting point (° C.) |
|---|---|---|---|---|---|---|---|
| 4 | H | $CF_3$ | $CH_3$ | F | CN | 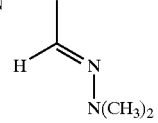 | 182 |

Starting Materials of the Formula (II)

Example (II-I)

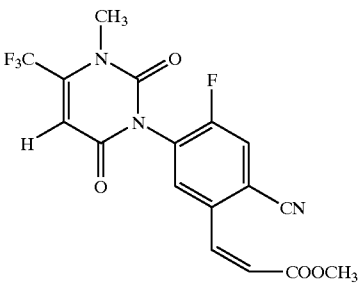

A mixture of 1.8 g (21 mmol) of methyl acrylate, 1.6 g (15.5 mmol) of t-butyl nitrite, 1.6 g (12 mmol) of copper(II) chloride and 50 ml of acetonitrile is cooled to approximately 0° C., and a solution of 3.3 g (10 mmol) of 1-(5-amino-4-cyano-2-fluoro-phenyl)-3,6-dihydro-2,6-dioxo-3-methyl-4-trifluoromethyl-1(2H)-pyrimidine in 20 ml of acetonitrile is added dropwise thereto at this temperature. The reaction mixture is then allowed to warm to room temperature and stirred at this temperature for 18 hours. The mixture is subsequently, after addition of 20 ml of 1N hydrochloric acid, extracted with ethyl acetate and the organic phase is dried with sodium sulphate and filtered. The filtrate is concentrated and the residue is worked up by column chromatography. This gives 2.8 g (65% of theory) of 1-[4-cyano-2-fluoro-5-(2-chloro-2-methoxycarbonyl-ethyl)-phenyl]-3,6-dihydro-2,6-dioxo-3-methyl-4-trifluoromethyl-1(2H)-pyrimidine of melting point 46° C.

0.22 g of sodium hydride (60% strength) are added with stirring to a mixture of 2.0 g (4.6 mmol) of 1-[4-cyano-2-fluoro-5-(2-chloro-2-methoxycarbonyl-ethyl)-phenyl]-3,6-dihydro-2,6-dioxo-3-methyl-4-trifluoromethyl-1(2H)-pyrimidine and 30 ml of N,N-dimethyl-formamide which had been cooled to 0° C., and the reaction mixture is stirred initially at 0° C. for 15 minutes, then at 20° C. for approximately 60 minutes and finally at 60° C. for 6 hours. The mixture is then concentrated under water pump vacuum, the residue is stirred with diisopropyl ether and the crystalline product is isolated by filtration with suction.

This gives 1.1 g (60% of theory) of 1-[4-cyano-2-fluoro-5-(2-methoxycarbonylethenyl)-phenyl]-3,6-dihydro-2,6-dioxo-3-methyl-4-trifluoromethyl-1(2H)-pyrimidine of melting point 154° C.

Starting Materials of the Formula (V)

Example (V-1)

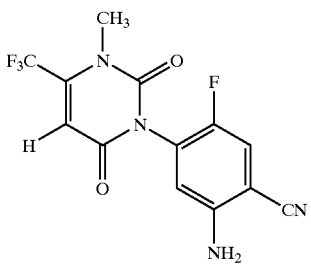

0.17 g (1.2 mmol) of pivaloyl chloride are added with stirring to a mixture of 0.50 g (1.2 mmol) of 1-(4-cyano-2-fluoro-5-trifluoroacetylamino-phenyl)-3,6-dihydro-2,6-dioxo-3-methyl-4-trifluoromethyl-1(2H)-pyrimidine, 1 ml of triethylamine and 50 ml of acetonitrile, and the reaction mixture is stirred at 20° C. for 18 hours and for a further 15 hours at 60° C. The mixture is then concentrated under water pump vacuum, the residue is shaken with 1N hydrochloric acid/ethyl acetate and the organic phase is separated off, dried with sodium sulphate and filtered. The filtrate is concentrated under water pump vacuum and the residue is worked up by column chromatography (silica gel, chloroform/ethyl acetate, vol.: 1:1).

In addition to unreacted 1-(4-cyano-2-fluoro-5-trifluoroacetylamino-phenyl)-3,6-dihydro-2,6-dioxo-3-methyl-4-trifluoromethyl-1(2H)-pyrimidine (first fraction: 0.30 g), 0.2 g (50% of theory) of 1-(4-cyano-2-fluoro-5-amino-phenyl)-3,6-dihydro-2,6-dioxo-3-methyl-4-trifluoromethyl-1(2H)-pyrimidine is obtained as second fraction.

Melting point: 195° C.

Use Examples

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of tile test plants are sown in normal soil. After 24 hours, this soil is sprayed with the preparation of active compound. It is advantageous to keep the amount of water per unit area constant. The concentration of active compound in the preparation is immaterial, only the amount of active compound applied per unit area matters.

After three weeks, the degree of damage to tile plants is rated in % damage in comparison with the development of the untreated control.

The figures denote:

0%=no effect (like untreated control)

100%=total destruction

In this test, at application rates between 30 and 125 g/ha, for example the compounds of Preparation Examples 1,2 and 4 exhibit very strong activity against weeds such as Amaranthus (95%), Sinapis (100%), Xanthium (100%), Digitaria (80 to 100%), Setaria (95 to 100%), Chenopodium (100%), Matricaria (100%) and Veronica (100%), and they are well tolerated by crop plants, such as, for example, maize, barley and cotton, (0 to 30%).

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular desired amounts of active compound per unit area. The concentration of the spray liquor is chosen so that the particular desired amounts of active compound are applied in 1000 l of water/ha.

After three weeks, the degree of damage to the plants is rated in % damage in comparison with the development of the untreated control.

The figures denote:

0%=no effect (like untreated control)

100%=total destruction

In this test, at application rates between 30 and 125 g/ha, for example the compounds of Preparation Examples 1, 2 and 4 exhibit very strong activity against weeds, such as Abutilon (100%), Amaranthus (100%), Galium (100%), Datura (100%), Polygonum (100%) and Solanum (100%), and some of them are well tolerated by crop plants, such as, for example, wheat (10%).

What is claimed is:

1. A process for preparing a substituted phenyluracil of the formula

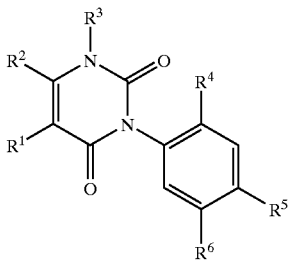

wherein
- $R^1$ represents a moiety selected from the group consisting of hydrogen; fluorine; chlorine; bromine; unsubstituted $C_1$ to $C_4$-alkyl; and, fluorine or chlorine-substituted $C_1$–$C_4$-alkyl;
- $R^2$ represents unsubstituted $C_1$–$C_4$-alkyl or fluorine- and/or chlorine-substituted $C_1$–$C_4$-alkyl;
- $R^3$ represents a moiety selected from the group consisting of hydrogen; amino; unsubstituted $C_1$–$C_6$-alkyl; cyano-, fluorine-, chlorine- or $C_1$–$C_4$-alkoxy-substituted $C_1$–$C_6$-alkyl; unsubstituted $C_2$–$C_6$-alkenyl or $C_2$–$C_6$-alkynyl; and, fluorine- and/or chlorine-substituted $C_2$–$C_6$-alkenyl or $C_2$–$C_6$-alkynyl;
- $R^4$ represents hydrogen, cyano, fluorine or chlorine,
- $R^5$ represents cyano or thiocarbamoyl, and
- $R^6$ represents one of the following groups:

 (1)

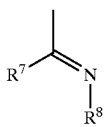 (2)

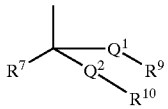 (3)

wherein $Q^1$ and $Q^2$ each represent oxygen or sulphur,
- $R^7$ represents a moiety selected from the group consisting of hydrogen; unsubstituted $C_1$–$C_4$-alkyl; and halogen- or $C_1$–$C_4$-alkoxy-substituted $C_1$–$C_4$-alkyl;
- $R^8$ represents a moiety selected from the group consisting of hydrogen; hydroxyl; amino; unsubstituted $C_1$–$C_6$-alkyl, $C_1$–$C_6$-alkoxy, $C_1$–$C_6$-alkylamino, di-($C_1$–$C_4$-alkyl)-amino, $C_1$$C_4$-alkylcarbonylamino or $C_1$–$C_4$-alkyl-sulphonylamino; $C_1$–$C_6$-alkyl, $C_1$–$C_6$-alkoxy, $C_1$–$C_6$-alkylamino, di-($C_1$–$C_4$-alkyl)-amino, $C_1$–$C_4$-alkylcarbonylamino or $C_1$–$C_4$-alkyl-sulphonylamino, each of which is substituted by halogen, $C_1$–$C_4$-alkoxy or $C_1$–$C_4$-alkoxy-carbonyl; unsubstituted $C_2$–$C_6$-alkenyl, $C_2$–$C_6$-alkenyloxy or $C_2$–$C_6$-alkinyl; $C_2$–$C_6$-alkenyl, $C_2$–$C_6$-alkenyloxy or $C_2$–$C_6$-alkinyl, each of which is substituted by halogen; $C_3$–$C_6$-cycloalkyl, $C_3$–$C_6$-cyclo-alkyloxy, $C_3$–$C_6$-cycloalkylamino, $C_3$–$C_6$-cycloalkyl-carbonyl-amino or $C_3$–$C_6$-cycloalkylsulphonylamino, each of which may be substituted by halogen or $C_1$–$C_4$-alkyl; and, phenyl, phenoxy, phenylamino, phenylcarbonylamino, phenylsulphonylamino, phenyl-$C_1$–$C_4$-alkyl, phenyl-$C_1$–$C_4$-alkoxy, phenyl-$C_1$–$C_4$-alkylamino, each of which may be substituted by halogen, $C_1$–$C_4$-alkyl, $C_1$–$C_4$-halogenoalkyl, $C_1$–$C_4$-alkoxy or $C_1$–$C_4$-halogenoalkoxy; and $R^9$ and $R^{10}$ each represent $C_1$–$C_4$-alkyl comprising:
(a) reacting a carbonyl phenyluracil of the formula (Ia)

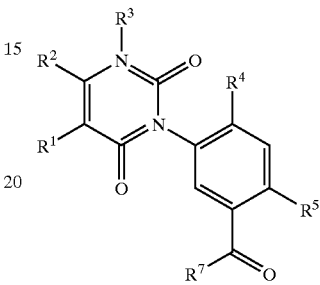 (Ia)

wherein
$R^1$, $R^2$, $R^3$, $R^4$, $R^5$ and $R^7$ are each as defined above with an amino compound of the general formula (III)

$$H_2N—R^8 \quad (III)$$

wherein
$R^8$ is as defined above or with acid adducts of compounds of the formula (III); or
(b) reacting a carbonylphenyluracil of the formula (Ia)

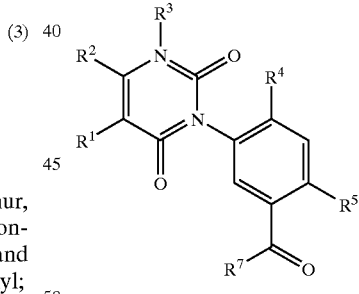 (Ia)

wherein
$R^1$, $R^2$, $R^3$, $R^4$, $R^5$ and $R^7$ are each as defined above with an alcohol and/or a mercaptan of the formula (IVa) or (IVb)

$HQ^1R^9$ (IVa)

$HQ^2R^{10}$ (IVb)

wherein
$Q^1$, $Q^2$, $R^9$ and $R^{10}$ are each as defined above.

* * * * *